US005140019A

United States Patent [19]
Wada et al.

[11] Patent Number: 5,140,019
[45] Date of Patent: Aug. 18, 1992

[54] STABILIZED AGROCHEMICAL COMPOSITIONS

[75] Inventors: Yuzuru Wada, Hachioji; Shigeharu Koyama, Oyama, both of Japan

[73] Assignee: Nihon Tokushu Noyaku Seizo K.K., Tokyo, Japan

[21] Appl. No.: 616,442

[22] Filed: Nov. 19, 1990

[30] Foreign Application Priority Data
Nov. 28, 1989 [JP] Japan .................................. 1-306650

[51] Int. Cl.$^5$ ................... A61K 31/435; A61K 31/00; C07D 401/06
[52] U.S. Cl. ...................................... 514/89; 514/75; 514/87; 514/94; 514/109; 546/278
[58] Field of Search ..................... 514/94, 109, 75, 87, 514/89; 546/278

[56] References Cited

U.S. PATENT DOCUMENTS

| 4,725,589 | 2/1988 | Tsuboi et al. | 514/128 |
| 4,780,457 | 10/1988 | Tsuboi et al. | 514/89 |

FOREIGN PATENT DOCUMENTS

| 7656587 | 2/1988 | Australia . | |
| 1164337 | 3/1984 | Canada | 514/89 |
| 0111843 | 6/1984 | European Pat. Off. . | |
| 0131735 | 1/1985 | European Pat. Off. . | |
| 0214546 | 3/1987 | European Pat. Off. . | |
| 0243694 | 11/1987 | European Pat. Off. . | |
| 0256407 | 2/1988 | European Pat. Off. . | |
| 2081905 | 12/1971 | France . | |
| 48-03476 | 9/1973 | Japan | 514/94 |
| 62-56408 | 3/1987 | Japan . | |
| 62-99312 | 5/1987 | Japan . | |
| 63-45209 | 2/1988 | Japan . | |
| 63-68507 | 3/1988 | Japan . | |
| 63-126810 | 5/1988 | Japan . | |
| 63-150205 | 6/1988 | Japan . | |
| 1415001 | 11/1975 | United Kingdom . | |

OTHER PUBLICATIONS

Shiokawa et al., Chemical Abstract, 108, 1988 #108; 21897m.
Chemical Patents Index Basic Abstracts Journal, Section C, Aug. 31, 1988, accession No. 88-188020/27 Derwent Publications Ltd., London, GB & JP.
Chemical Patents Index, Basic Abstracts Journal, Section C. Nov. 16, 1987, accession No. 87-260900/37 Derwent Publication Ltd. London, GB & JP.
Central Patents Index, 1972 accession No. 72-73896T/46, Derwent Publications Ltd. London, GB & JP.
Chemical Patents Index, Basic Abstracts Journal Section C AGDOC Mar. 8, 1989 accession No. 89-01333/02, Derwent Publications Ltd. London GB & JP.

Primary Examiner—Mukund J. Shah
Assistant Examiner—Y. N. Gupta
Attorney, Agent, or Firm—Sprung Horn Kramer & Woods

[57] ABSTRACT

Compositions which contain, as the active ingredients, a combination of heterocyclic compounds of the general formula (I) and organophosphorous compounds, in addition to one or more compounds having a polyethyleneglycol or polypropyleneglycol chain or an ethyleneglycol-propyleneglycol copolymeric chain, or a mixture of these compounds which results in a stabilization of the active ingredients without any adverse influences on the physical properties of the formulations.

9 Claims, No Drawings

STABILIZED AGROCHEMICAL COMPOSITIONS

The present invention relates to novel stabilized agrochemical compositions, and the preparation and the use thereof.

It is known from the disclosures of Japanese Patent Laid-open No. 56408-1987, No. 45209-1988 and No. 126810-1988 that a mixed agent, which contains as active ingredients, a mixture of compounds of the general formula (I) with organophosphorous compounds is effective as an insecticide for agricultural and horticultural use. In addition, Japanese Patent Laid-open No. 99312-1987, No. 68507-1988 and No. 150205-1988 disclose that such a mixed agent is effective not only as an insecticidal agent but also as a fungicidal agent for agricultural and horticultural use.

In these Japanese patent specifications, it is stated that such a mixed agent can exhibit excellent cooperative and synergistic actions over the individual activities of respective components.

However, the Applicant has now found that, when a mixed agent is prepared by mixing compounds of the general formula (I) with organophosphorous compounds, then the mixed agent is rather unstable and cannot be stored for a virtually long time, because the two active components contained in the mixed agent interact with each other, so that a decomposition of these components each is promoted. Thus, the decomposition rate of each component contained in the mixed agent is far higher than that of each component contained in a single active ingredient preparation.

So, it is highly desired to offer a substantial improvement on the stability of the mixed agent.

Accordingly, the invention relates to a stabilized agrochemical composition comprising, as active ingredients, a combination of:

(A) heterocyclic compounds represented by the general formula:

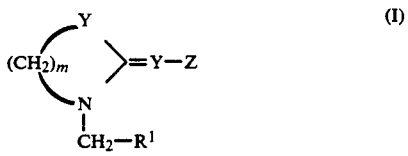

wherein X represents S, $CH_2$ or $N-R^2$, wherein $R^2$ represents hydrogen atom or alkylcarbonyl group;

$R^1$ represents pyridyl group, which is optionally substituted by at least one substituent selected from the class consisting of halogen atoms and alkyl groups, or thiazolyl group, which is optionally substituted by at least one substituent selected from the class consisting of halogen atoms and alkyl groups;

m is 2 or 3;

Y represents N or CH; and

Z represents $NO_2$ or CN; and (B) organophosphorous compounds, characterized in that the composition further contains one or more compounds having a polyethyleneglycol or polypropyleneglycol chain or an ethyleneglycol-propyleneglycol copolymeric chain, or a mixture of these compounds.

Also, the invention relates to a method of preparing a stabilized agrochemical composition, which contains, as active ingredients, a combination of heterocyclic compounds of the general formula (I) and organophosphorous compounds, characterized in that the composition is stabilized by adding thereto one or more compounds having a polyethyleneglycol, polypropyleneglycol chain or a ethyleneglycol-propyleneglycol copolymeric chain, or a mixture of these compounds.

It has been found that the agrochemical compositions according to the invention can be used in various agricultural and horticultural fields.

Surprisingly, it has been found that, in the present compositions which contain, as the active ingredients, a combination of heterocyclic compounds of the general formula (I) and organophosphorous compounds, the addition of one or more compounds having a polyethyleneglycol or polypropyleneglycol chain or an ethyleneglycol-propyleneglycol copolymeric chain, or a mixture of these compounds results in a stabilization of the active ingredients without any adverse influences on the physical properties of the formulations. On the basis of this finding, the invention has been completed.

Consequently, the stabilized agrochemical compositions according to the invention provide an excellent technique in the manufacturing industry of agricultural chemicals, and are worthy of an extremely excellent technical advancement of industrial utility.

In the stabilized agrochemical compositions according to the invention, use is made of heterocyclic compounds of the formula (I). Examples of the heterocyclic compounds useful as components of the composition of the present invention are:

1-(3-pyridylmethyl)-2-(nitromethylene)tetrahydropyrimidine, 1-(2-methyl-5-pyridylmethyl)-2-(nitromethylene)imidazolidine, 1-(2-methyl-5-pyridylmethyl)-2-(nitromethylene)tetrahydropyrimidine, 1-(2-methoxy-5-pyridylmethyl)-2-(nitromethylene)imidazolidine, 1-(2-methoxy-5-pyridylmethyl)-2-(nitromethylene)tetrahydropyrimidine, 1-(2-chloro-5-pyridylmethyl)-2-(nitromethylene)imidazolidine, 1-(2-chloro-5-pyridylmethyl)-2-(nitromethylene)tetrahydropyrimidine, 1-(2-fluoro-5-pyridylmethyl)-2-(nitromethylene)imidazolidine, 1-(2-fluoro-5-pyridylmethyl)-2-(nitromethylene)tetrahydropyrimidine, 1-(2-bromo-5-pyridylmethyl)-2-(nitromethylene)imidazolidine, 1-(2-bromo-5-pyridylmethyl)-2-(nitromethylene)tetrahydropyrimidine, 1-(5-chloro-2-pyridylmethyl)-2-(nitromethylene)imidazolidine, 1-(5-chloro-2-pyridylmethyl)-2-(nitromethylene)tetrahydropyrimidine, 1-(2,4-dichloro-5-pyridylmethyl)-2-(nitromethylene)tetrahydropyrimidine, 1-(2,4-dibromo-5-pyridylmethyl)-2-(nitromethylene)imidazolidine, 1-(2,3-dichloro-5-pyridylmethyl)-2-(nitromethylene)imidazolidine, 1-(3-pyridylmethyl)-2-(nitromethylene)tetrahydropyrimidine hydrochloride, 1-(2-methyl-5-pyridylmethyl)-2-(nitromethylene)tetrahydropyrimidine p-toluenesulfonate, 1-(2-methoxy-5-pyridylmethyl)-2-(nitromethylene)tetrahydropyrimidine succinate, 1-(2-chloro-5-pyridylmethyl)-2-(nitromethylene)imidazolidine hydrochloride,
1-(2-fluoro-5-pyridylmethyl)-2-(nitromethylene)tetrahydropyrimidine-cupric acetate,
1-(2-bromo-5-pyridylmethyl)-2-(nitromethylene)imidazolidine succinate,
1-(2,4-dichloro-5-pyridylmethyl)-2-(nitromethylene)tetrahydropyrimidine p-toluenesulfonate,
3-(3-pyridylmethyl)-2-(nitromethylene)thiazolidine,
3-(2-chloro-5-pyridylmethyl)-2-(nitromethylene)thiazolidine,
3-(2-chloro-5-pyridylmethyl)-2-(nitromethylene)tetrahydro-2H-1,3-thiazine,
3-(2-bromo-5-pyridylmethyl)-2-(nitromethylene)thiazolidine,
3-(2-bromo-5-pyridylmethyl)-2-(nitromethylene)tetrahydro-2H-1,3-thiazine,
3-(2-fluoro-5-pyridylmethyl)-2-(nitromethylene)thiazolidine,
3-(2-fluoro-5-pyridylmethyl)-2-(nitromethylene)tetrahydro-2H-1,3-thiazine,
3-(2,4-dichloro-5-pyridylmethyl)-2-(nitromethylene)tetrahydro-2H-1,3-thiazine,
3-(2-methyl-5-pyridylmethyl)-2-(nitromethylene)thiazolidine,
3-(2-methyl-5-pyridylmethyl)-2-(nitromethylene)tetrahydro-2H-1,3-thiazine,
3-(2-methoxy-5-pyridylmethyl)-2-(nitromethylene)tetrahydro-2H-1,3-thiazine,
1-(3-pyridylmethyl)-2-(nitroimino)imidazolidine,
1-(2-chloro-5-pyridylmethyl)-2-(nitroimino)imidazolidine,
1-(2-chloro-5-pyridylmethyl)-2-(nitroimino)tetrahydropyrimidine,
1-(2-fluoro-5-pyridylmethyl)-2-(nitroimino)imidazolidine,
1-(2-fluoro-5-pyridylmethyl)-2-(nitroimino)tetrahydropyrimidine,
1-(2-bromo-5-pyridylmethyl)-2-(nitroimino)imidazolidine,
1-(2,3-dichloro-5-pyridylmethyl)-2-(nitroimino)imidazolidine,
1-(2-methyl-5-pyridylmethyl)-2-(nitroimino)imidazolidine,
1-(2-methyl-5-pyridylmethyl)-2-(nitroimino)tetrahydropyrimidine,
1-(2-chloro-5-thiazolylmethyl)-2-(nitroimino)imidazolidine,
1-(2-chloro-5-thiazolylmethyl)-2-(nitroimino)tetrahydropyrimidine,
1-(2-fluoro-5-thiazolylmethyl)-2-(nitroimino)imidazolidine,
1-(2-methyl-5-thiazolylmethyl)-2-(nitroimino)imidazolidine,
1-(2-methyl-5-thiazolylmethyl)-2-(nitroimino)tetrahydropyrimidine,
1-acetyl-3-(2-chloro-5-pyridylmethyl)-2-(nitroimino)imidazolidine,
1-acetyl-3-(2-chloro-5-pyridylmethyl)-2-(nitroimino)tetrahydropyrimidine,
1-butyryl-3-(2-chloro-4-fluoro-5-pyridylmethyl)-2-(nitroimino)imidazolidine,
3-(2-chloro-5-pyridylmethyl)-2-(nitroimino)thiazolidine,
3-(2-chloro-5-pyridylmethyl)-2-(nitroimino)tetrahydro-2H-1,3-thiazine,
3-(2-fluoro-5-pyridyl)-2-(nitroimino)thiazolidine,
1-(2-chloro-5-pyridylmethyl)-2-(nitroimino)pyrrolidine,
1-(2-chloro-5-pyridylmethyl)-2-(nitroimino)piperidine,
1-(2-bromo-5-pyridyl)-2-(nitroimino)pyrrolidine,
1-(2-fluoro-5-pyridylmethyl)-2-(nitroimino)pyrrolidine,
1-(2-chloro-5-pyridylmethyl)-2-(cyanoimino)imidazolidine,
1-(2-chloro-5-pyridylmethyl)-2-(cyanoimino)tetrahydropyrimidine,
1-(2-fluoro-5-pyridylmethyl)-2-(cyanoimino)imidazolidine,
1-(2-bromo-5-pyridylmethyl)-2-(cyanoimino)imidazolidine,
1-(2-methyl-5-pyridylmethyl)-2-(cyanoimino)imidazolidine,
1-(2-methyl-5-pyridylmethyl)-2-(cyanoimino)tetrahydropyrimidine,
1-(2-chloro-5-thiazolylmethyl)-2-(cyanoimino)imidazolidine,
1-(2-chloro-5-thiazolylmethyl)-2-(cyanoimino)tetrahydropyrimidine,
1-(2-fluoro-5-thiazolylmethyl)-2-(cyanoimino)tetrahydropyrimidine,
1-(2-chloro-5-pyridylmethyl)-2-(cyanoimino)thiazolidine,
1-(2-chloro-5-pyridylmethyl)-2-(cyanoimino)tetrahydro-2H-1,3-thiazine,
1-(2-fluoro-5-pyridylmethyl)-2-(cyanoimino)thiazolidine,
1-(2-chloro-5-thiazolylmethyl)-2-(cyanoimino)thiazolidine,
1-(2-chloro-5-thiazolylmethyl)-2-(cyanoimino)tetrahydro-2H-1,3-thiazine, and the like.

The stabilized agricultural chemical compositions contain organophosphorous compounds as one of the two active ingredients. The term "organophosphorous compounds" means active compounds which can generally be used in the fields of plant protection. These compounds are preferably insecticides, fungicides, and the like. Examples of the active "organophosphorous compounds" of this type are as follows:

O-ethyl S,S-diphenyl phosphorodithioate ("edifenphos"),
S-benzyl O,O-diisopropyl phosphorothioate ("IBP"),
O,O-dimethyl O-4-methylthio-m-tolyl phosphorothioate ("fenthion"),
O,O-dimethyl O-4-nitro-m-tolyl phosphorothioate ("fenitrothion"),
O,O-dimethyl O-3,5,6-trichloro-2-pyridyl phosphorothioate ("chlorpyrifos-methyl"),
S-1,2-bis(ethoxycarbonyl)ethyl O,O-dimethyl phosphorodithioate ("malathon"),
S-α-ethoxycarbonylbenzyl O,O-dimethyl phosphorodithioate ("phenthoate"),
dimethyl 2,2,2-trichloro-1-hydroxyethyl phosphonate ("trichlofon"),
O-2,4-dichlorophenyl O-ethyl S-propyl phosphorodithioate ("prothiofos"),
O-ethyl O-4-methylthiophenyl S-propyl phosphorodithioate ("sulprofos"),
S-2-ethylsulfinyl-1-methylethyl O,O-dimethyl phosphorothioate ("oxydeprofos"),
O,O-dimethyl S-2-ethylthioethyl phosphorodithioate ("disulfoton"),
2,2-dichlorovinyl dimethyl phosphate ("dichlorvos"),
(Z)-2-chloro-1-(2,4,5-trichlorophenyl) vinyl dimethyl phosphate ("tetrachlorvinphos"),
O,O-diethyl O-2-isopropyl-6-methylpyrimidin-4-yl phosphorothioate ("diazinon"), 2,3-dihydro-3-oxo-2-phenyl-6-pyridazinyl diethyl phosphorothioanate ("pyridaphenthion"), and O-ethyl O-2-isopropoxycarbonylphenyl-isopropyl phosphoroamidothioate ("isofenphos").

As the stabilizers for the present agrochemical compositions, there may be mentioned a certain kind of compounds having a polyethyleneglycol chain, a polypropyleneglycol chain or an ethyleneglycol-propyleneglycol copolymeric chain. Examples of such compounds are polyoxyethylene-alkylethers, polyoxyethylene-alkylarylethers, polyoxypropylene-alkylethers, polyoxypropylene-alkylarylethers, polyoxyethylene-polyoxypropylene block polymers, polyethyleneglycols, polypropyleneglycols and the like.

The compounds, having a polyethyleneglycol, polypropyleneglycol or ethyleneglycol-propyleneglycol copolymeric chain, employed as the stabilizers according to the invention, exhibit a satisfactory stabilization effect on the combination of the active ingredients contained in the present agricultural chemical compositions, without any adverse influence on the physical properties of the formulations.

The present agrochemical compositions may be prepared by a process, wherein the mixed active ingredients are admixed with one or more compounds having a polyethyleneglycol or polypropyleneglycol chain or an ethyleneglycol-propyleneglycol copolymeric chain, and also with solid carriers and optionally with surface active agents, in a conventional manner customarily employed in the production of agricultural chemicals. The compositions according to the invention may be converted into various formulations.

As solid diluents there may be used powders and granules of plants; and ground minerals such as clays (e.g. kaolinite, montmorillonite and attapulgite), talc, pyrophyllite, mica, calcite, vermiculite, dolomite, apatite, and diatomaceous earth; synthetic inorganic materials, for instance, synthetic alumina; synthetic resins such as phenol resins, urea resins, polyvinyl chlorides, and the like.

As surface active agents, use may be made of anionic surface active agents such as alkyl sulfates, for instance, sodium lauryl sulfate, aryl sulfonates, for example, alkyl aryl sulfonates and sodium alkyl naphthalene sulfonates; polycarboxylate salts such as sodium salts of maleic acid-olefin copolymers; nonionic surface active agents, for instance, esters of polyhydric alcohols, e.g. aliphatic esters of glycerol, aliphatic esters of sorbitan, and the like.

In the compositions according to the invention, it is also possible to use adhesives such as carboxymethyl cellulose and natural and synthetic polymers, for instance, gum arabic, polyvinyl alcohol, polyvinyl acetate, etc.

It is possible to use colorants such as inorganic pigments, for instance, iron oxide, titanium oxide and Prussian Blue; and organic dyestuffs such as alizarin dyestuffs, azo dyestuffs and metal phthalocyanine dyestuffs; and trace elements such as iron, manganese, boron, copper, cobalt, molybdenum and zinc.

As mentioned above, the stabilized agrochemical compositions according to the invention can be converted into formulations including powders, wettable powders, granules and the like.

In general, the formulations contain from 0.05 to 95% by weight of active compound, and preferably from 0.1 to 80% by weight thereof.

The compounds, having a polyethyleneglycol or polypropyleneglycol chain or an ethyleneglycol-propyleneglycol copolymeric chain, may be added to the present compositions in an amount of from 0.1 to 30% by weight, preferably from 0.5 to 15% by weight, in the case where the compositions are used in the form of ordinary formulations. For example, in the case of powder formulations, the amount is from 0.1 to 20% by weight, preferably from 0.5 to 10% by weight. In the case of wettable powders, the amount is from 0.1 to 30% by weight, preferably from 1.0 to 15% by weight. In the case of granules, the amount is from 0.1 to 30% by weight, preferably from 0.5 to 15% by weight.

In the agrochemical compositions according to the invention, it is possible to optionally use other known components such as fungicides, bactericides, insecticides, acaricides, herbicides, bird repellents, growth regulators, fertilizers and/or soil improvers. Examples of other insecticides are carbamate compounds, carboxylate compounds, chlorinated hydrocarbon compounds, and microbial insecticides.

The invention will be further illustrated by way of Examples. However, it should be noted that the scope of the invention is not limited only to these Examples.

EXAMPLES

Active ingredients under tests:
The heterocyclic compound of the general formula (I):
1-(2-chloro-5-pyridylmethyl)-2-(nitroimino)-imidazolidine ("imidacloprid")
The organophosphorous compounds:
O-ethyl S,S-diphenyl phosphorodithioate ("edifenphos"); and
O,O-dimethyl O-4-methylthio-m-tolyl phosphorothioate ("fenthion")

|  | Parts by weight |
|---|---|
| Example 1 (powder) | |
| imidacloprid | 1.0 |
| edifenphos | 2.5 |
| polyoxyethylene nonylphenylether | 2.0 |
| amorphous silica hydrate | 5.0 |
| clay | 89.5 |
| Comparative Example 1 (powder) | |
| imidacloprid | 1.0 |
| edifenphos | 2.5 |
| amorphos silica hydrate | 5.0 |
| clay | 91.5 |
| Example 2 (powder) | |
| imidacloprid | 1.0 |
| fenthion | 2.5 |
| polyoxyethylene nonylphenylether | 2.0 |
| amorphous silica hydrate | 5.0 |
| clay | 89.5 |
| Comparative Example 2 (powder) | |
| imidacloprid | 1.0 |
| fenthion | 2.5 |
| amorphous silica hydrate | 5.0 |
| clay | 91.5 |

In each example, these components were pulverized and mixed with one another to form the aimed powder formulation.

TEST 1

Stability test of powder formulations:
The formulations thus prepared were placed in glass containers and stored in a dark room at a temperature of 40° C. for a period of time of 60 days. After that, a measurement was made about the decomposition rate of the active ingredients contained in the formulations.

The test results are shown in Table 1.

TABLE 1

|  | Decomposition rate (%), 40° C., 60 days | | |
|---|---|---|---|
|  | Imidacloprid | Edifenphos | Fenthion |
| Example 1 | 5.2 | 6.8 | — |
| Example 2 | 5.9 | — | 6.6 |
| Comparative Example 1 | 18.7 | 14.3 | — |
| Comparative Example 2 | 21.7 | — | 16.3 |

|  | Parts by weight |
|---|---|
| Example 3 (wettable powder) | |
| imidacloprid | 10.0 |
| edifenphos | 10.0 |
| polyoxyethylene nonylphenylether | 4.0 |
| sodium ligninsulfonate | 5.0 |
| amorphous silica hydrate | 18.0 |
| clay | 53.0 |
| Comparative Example 3 (wettable powder) | |
| imidacloprid | 10.0 |
| edifenphos | 10.0 |
| sodium ligninsulfonate | 5.0 |
| amorphous silica hydrate | 18.0 |
| clay | 57.0 |
| Example 4 (wettable powder) | |
| imidacloprid | 10.0 |
| fenthion | 10.0 |
| polyoxyethylene nonylphenylether | 4.0 |
| sodium ligninsulfonate | 5.0 |
| amorphous silica hydrate | 18.0 |
| clay | 53.0 |
| Comparative Example 4 (wettable powder) | |
| imidacloprid | 10.0 |
| fenthion | 10.0 |
| sodium ligninsulfonate | 5.0 |
| amorphous silica hydrate | 18.0 |
| clay | 57.0 |

In each example, the components were pulverized and mixed with one another to form the aimed formulation.

TEST 2

Stability test of wettable powder formulations:

The wettable powder formulations thus prepared were placed in glass containers, and stored in a dark room at a temperature of 40° C. for a period of time of 60 days. The results are shown in Table 2.

TABLE 2

|  | Decomposition rate (%), 40° C., 60 days | | |
|---|---|---|---|
|  | Imidacloprid | Edifenphos | Fenthion |
| Example 3 | 5.5 | 7.0 | — |
| Example 4 | 5.2 | — | 6.2 |
| Comparative Example 3 | 16.2 | 15.8 | — |
| Comparative Example 4 | 17.2 | — | 11.8 |

|  | Parts by weight |
|---|---|
| Example 5 (granules) | |
| imidacloprid | 2.0 |
| fenthion | 3.0 |
| polyoxyethylene nonylphenylether | 2.0 |
| amorphous silica hydrate | 5.0 |
| bentonite | 35.0 |
| clay | 53.0 |
| Comparative Example 5 (granules) | |
| imidacloprid | 2.0 |
| fenthion | 3.0 |
| amorphous silica hydrate | 5.0 |
| bentonite | 35.0 |
| clay | 55.0 |

In these examples each, the granular formulation was prepared by a process, wherein the components were mixed and kneaded together, and the resultant mixture was extruded to form the granules.

TEST 3

Stability test of granular formulations:

The granular formulations thus prepared were placed in glass containers, and stored in a dark room at a temperature of 40° C. for 60 days. After that, a measurement was made about the decomposition rate of the active ingredients. The test results are shown in Table 3.

TABLE 3

|  | Decomposition rate (%), 40° C., 60 days | |
|---|---|---|
|  | Imidacloprid | Fenthion |
| Example 5 | 3.9 | 4.7 |
| Comparative Example 5 | 18.3 | 13.4 |

Also, in the case of the active compounds, each of the general formula (I), shown below, it has been observed that a mixture of the compounds of the general formula (I) with active organophosphorous compounds selected from the class consisting of edifenphos, fenthion, chlorpyrifos-methyl, prothiofos, sulprofos, disulfoton, tetrachlorvinphos and pyridaphenthion, can be formulated into a composition having a satisfactory stability according to the invention.

1-(2-methyl-5-pyridylmethyl)-2-(nitromethylene)tetrahydropyrimidine, 1-(2-methoxy-5-pyridylmethyl)-2-(nitromethylene)tetrahydropyrimidine, 1-(2-bromo-5-pyridylmethyl)-2-(nitromethylene)tetrahydropyrimidine, 1-(2-chloro-5-pyridylmethyl)-2-(nitromethylene)imidazolidine, 1-(2-fluoro-5-pyridylmethyl)-2-(nitromethylene)imidazolidine, 3-(2-chloro-5-pyridylmethyl)-2-(nitromethylene)thiazolidine, 3-(2-chloro-5-pyridylmethyl)-2-(nitromethylene)tetrahydro-2H-1,3-thiazine, 1-(2-chloro-5-pyridylmethyl)-2-(nitroimino)tetrahydropyrimidine, 1-(2-chloro-5-thiazolylmethyl)-2-(nitroimino)imidazolidine, 1-acetyl-3-(2-chloro-5-pyridylmethyl)-2-(nitroimino)imidazolidine, 3-(2-chloro-5-pyridylmethyl)-2-(nitroimino)thiazolidine, 1-(2-chloro-5-pyridylmethyl)-2-(nitroimino)piperidine, and 1-(2-chloro-5-pyridylmethyl)-2-(cyanoimino)imidazolidine.

What is claimed:

1. A stabilized agrochemical composition comprising, as active ingredients, a combination of:

(A) heterocyclic compounds represented by the general formula:

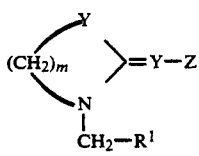

wherein X represents N—R$^2$, wherein R$^2$ represents hydrogen atom or alkylcarbonyl group;

R$^1$ represents pyridyl group which is optionally substituted by at least one substituent selected from the class consisting of halogen atoms and alkyl groups, m is 2;

Y represents N or CH; and

Z represents NO$_2$ or CN; and (B) Organophosphorous compounds, characterized in that the composition further contains as a stabilizer (C) one or more compounds having a polyethyleneglycol or polypropyleneglycol chain or an ethyleneglycol-propyleneglycol copolymeric chain, or a mixture of these compounds.

2. A stabilized agrochemical composition according to claim 1 wherein the heterocycle compound of Formula I is selected from the group comprising:

1-(2-methyl-5-pyridylmethyl)-2-(nitromethylene)imidazolidine,
1-(2-methoxy-5-pyridylmethyl)-2-(nitromethylene)imidazolidine,
1-(2-chloro-5-pyridylmethyl)-2-(nitromethylene)imidazolidine,
1-(2-fluoro-5-pyridylmethyl)-2-(nitromethylene)imidazolidine,
1-(2-bromo-5-pyridylmethyl)-2-(nitromethylene)imidazolidine,
1-(5-chloro-2-pyridylmethyl)-2-(nitromethylene)imidazolidine,
1-(2,4-dibromo-5-pyridylmethyl)-2-(nitromethylene)imidazolidine,
1-(2,3-dichloro-5-pyridylmethyl)-2-(nitromethylene)imidazolidine,
1-(2-chloro-5-pyridylmethyl)-2-(nitromethylene)imidazolidine hydrochloride,
1-(2-bromo-5-pyridylmethyl)-2-(nitromethylene)imidazolidine succinate,
1-(3-pyridylmethyl)-2-(nitroimino)imidazolidine,
1-(2-chloro-5-pyridylmethyl)-2-(nitroimino)imidazolidine,
1-(2-fluoro-5-pyridylmethyl)-2-(nitroimino)imidazolidine,
1-(2-bromo-5-pyridylmethyl)-2-(nitroimino)imidazolidine,
1-(2,3-dichloro-5-pyridylmethyl)-2-(nitroimino)imidazolidine,
1-(2-methyl-5-pyridylmethyl)-2-(nitroimino)imidazolidine,
1-(2-chloro-5-thiazolylmethyl)-2-(nitroimino)imidazolidine,
1-(2-fluoro-5-thiazolylmethyl)-2-(nitroimino)imidazolidine,
1-(2-methyl-5-thiazolylmethyl)-2-(nitroimino)imidazolidine,
1-acetyl-3-(2-chloro-5-pyridylmethyl)-2-(nitroimino)imidazolidine,
1-butyryl-3-(2-chloro-4-fluoro-5-pyridylmethyl)-2-(nitroimino)imidazolidine,
1-(2-chloro-5-pyridylmethyl)-2-(cyanoimino)imidazolidine,
1-(2-fluoro-5-pyridylmethyl)-2-(cyanoimino)imidazolidine,
1-(2-bromo-5-pyridylmethyl)-2-(cyanoimino)imidazolidine,
1-(2-methyl-5-pyridylmethyl)-2-(cyanoimino)imidazolidine,
1-(2-chloro-5-thiazolylmethyl)-2-(cyanoimino)imidazolidine.

3. A stabilized agrochemical composition according to claim 1 wherein the organophosphorous compound is selected from the group comprising:

O-ethyl S,S-diphenyl phosphorodithioate ("edifenphos"),
S-benzyl O,O-diisopropyl phosphorothioate ("IBP"),
O,O-dimethyl O-4-methylthio-m-tolyl phosphorothioate ("fenthion"),
O,O-dimethyl O-4-nitro-m-tolyl phosphorothioate ("fenitrothion"),
O,O-dimethyl O-3,5,6-trichloro-2-pyridyl phosphorothioate ("chlorpyrifos-methyl"),
S-1,2-bis(ethoxycarbonyl)ethyl O,O-dimethyl phosphorodithioate ("malathon"),
S-α-ethoxycarbonylbenzyl O,O-dimethyl phosphorodithioate ("phenthoate"),
dimethyl 2,2,2-trichloro-1-hydroxyethyl phosphonate ("trichlofon"),
O-2,4-dichlorophenyl O-ethyl S-propyl phosphorodithioate ("prothiofos"),
O-ethyl O-4-methylthiophenyl S-propyl phosphorodithioate ("sulprofos"),
S-2-ethylsulfinyl-1-methylethyl O,O-dimethyl phosphorothioate ("oxydeprofos"),
O,O-dimethyl S-2-ethylthioethyl phosphorodithioate ("disulfoton"),
2,2-dichlorovinyl dimethyl phosphate ("dichlorvos"),
(Z)-2-chloro-1-(2,4,5-trichlorophenyl) vinyl dimethyl phosphate ("tetrachlorvinphos"),
O,O-diethyl O-2-isopropyl-6-methylpyrimidin-4-yl phosphorothioate ("diazinon"),
2,3-dihydro-3-oxo-2-phenyl-6-pyridazinyl diethyl phosphorothionate ("pyridaphenthion"), and
O-ethyl O-2-isopropoxycarbonylphenyl-isopropyl phosphoroamidothioate ("isofenphos").

4. A stabilized agrochemical composition according to claim 1 wherein the stabilizer component (C) is selected from the group comprising polyoxyethylene-alkylethers, polyoxyethylene-alkylarylethers, polyoxypropylene-alkylethers, polyoxypropylene-alkylarylethers, polyoxyethylene-polyoxypropylene block polymers, polyethyleneglycols, polypropyleneglycols and the like.

5. A stabilized agrochemical composition according to claim 1 wherein the active compounds (A) and (B) are present in an amount of from about 0.05 to about 95% by weight.

6. A stabilized agrochemical composition according to claim 1 wherein the active compounds (A) and (B) are present in an amount of from about 0.1 to 80% by weight.

7. A stabilized agrochemical composition according to claim 1 wherein the stabilizer (C) is present in an amount of from about 0.1 to about 30% by weight.

8. A stabilized agrochemical composition according to claim 1 wherein the stabilizer (C) is present in an amount from about 0.5 to about 15% by weight.

9. A method of preventing the decomposition of a mixed agrochemical composition comprising as active ingredients heterocyclic compounds according to Formula I, and organophosphorous compounds, comprising adding thereto an effective amount of one or more compounds having a polyethyleneglycol or polypropyleneglycol chain or an ethyleneglycol-propyleneglycol copolymeric chain, or a mixture of these compounds.

* * * * *

UNITED STATES PATENT AND TRADEMARK OFFICE
CERTIFICATE OF CORRECTION

PATENT NO. : 5,140,019
DATED : August 18, 1992
INVENTOR(S) : Wada, et al.

It is certified that error appears in the above-indentified patent and that said Letters Patent is hereby corrected as shown below:

Col. 1, line 42    Delete " 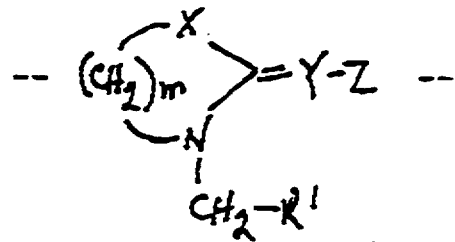 " and substitute

-- 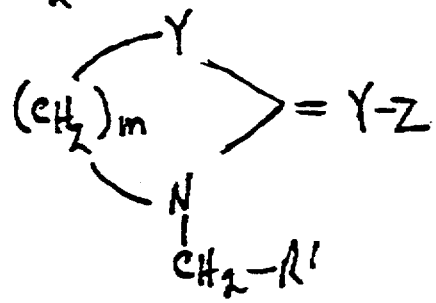 --

Col. 9, line 2    Delete " 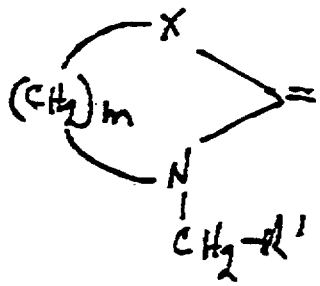 " and substitute -- 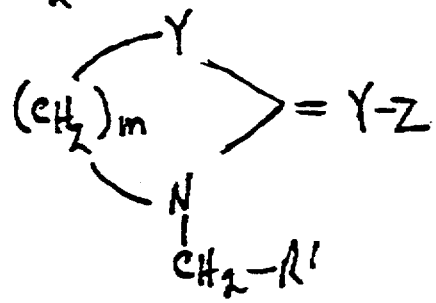 --

UNITED STATES PATENT AND TRADEMARK OFFICE
CERTIFICATE OF CORRECTION

PATENT NO. : 5,140,019

DATED : August 18, 1992

INVENTOR(S) : Wada, et al.

It is certified that error appears in the above-identified patent and that said Letters Patent is hereby corrected as shown below:

Col. 9, lines 61-64    Delete " 1-(2-chloro-5-thiazolylmethyl)-2-(nitroimino) imidazolidine, 1-(2-fluoro-5-thiazolylmethyl)-2-(nitroimino) imidazolidine, Col. 10, lines 11-12    Delete " 1-(2-chloro-5-thiazolylmethyl)-2-(cyanoimino)imidazolidine "

Signed and Sealed this

Eighth Day of November, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,140,019
DATED : August 18, 1992
INVENTOR(S) : Wada, et al.

It is certified that error appears in the above-indentified patent and that said Letters Patent is hereby corrected as shown below:

Col. 9, lines 31-32    Delete " 1-(2-methoxy-5-pyridylmethyl)-2-(nitromethylene)imidazolidine, "

Col. 9, lines 65-66    Delete " 1-(2-methyl-5-thiazolylmethyl)-2-(nitroimino)imidazolidine, "

Signed and Sealed this

Thirty-first Day of October 1995

Attest:

BRUCE LEHMAN

Attesting Officer    Commissioner of Patents and Trademarks